United States Patent [19]

Chan

[11] 4,018,920
[45] Apr. 19, 1977

[54] 3-HALOHYDROCARBYLTHIO-1,2,3-BENZOXATHIAZIN-4-(3H)-ONE 2-OXIDES

[75] Inventor: David Cheong King Chan, San Francisco, Calif.

[73] Assignee: Chevron Research Company, San Francisco, Calif.

[22] Filed: Apr. 1, 1976

[21] Appl. No.: 672,683

[52] U.S. Cl. .......................... 424/246; 260/243 R
[51] Int. Cl.² ............... C07D 291/08; A01N 9/14; A01N 15/00
[58] Field of Search ............ 260/243 R; 424/246

[56] References Cited

UNITED STATES PATENTS 3,780,030  12/1973  Morris .................. 260/243 R

Primary Examiner—John M. Ford
Attorney, Agent, or Firm—J. A. Buchanan, Jr.; Dix A. Newell; T. G. DeJonghe

[57] ABSTRACT

Compounds of the formula

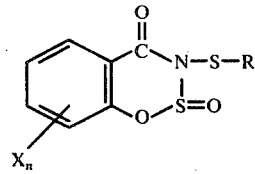

wherein R is an alkyl group or an alkenyl group, each substituted with 1 to 5 halogen atoms of atomic number 9 to 35, and X is halogen of atomic number 9 to 35, nitro, cyano, lower alkyl, lower alkoxy or trifluoromethyl and $n$ is 0 or an integer of 1 to 3, possess fungicidal activity.

7 Claims, No Drawings

3-HALOHYDROCARBYLTHIO-1,2,3-BENZOXA-THIAZIN-4-(3H)-ONE 2-OXIDES

BACKGROUND OF THE INVENTION

1. Field of the Invention

The present invention is directed to 3-haloalkylthio or haloalkenylthio 1,2,3-benzoxathiazin-4-(3H)-one 2-oxides and their use as fungicides.

2. Prior Art

U.S. Pat. No. 3,780,030 discloses 1,2,3-benzoxathiazin-4-(3H)-one 2-oxides and their use as antimicrobial compounds.

DESCRIPTION OF THE INVENTION

The compounds of the present invention are represented by the formula

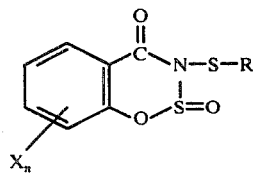

wherein R is an alkyl group of 1 to 3 carbon atoms substituted with 1 to 5 halogen atoms of atomic number 9 to 35 (i.e., fluorine, chlorine or bromine) or an alkenyl group of 2 to 3 carbon atoms substituted with 1 to 5 halogen atoms of atomic number 9 to 35 (fluorine, chlorine or bromine); X is halogen of atomic number 9 to 35, nitro, cyano, lower alkyl (1 to 4 carbon atoms), lower alkoxy (1 to 4 carbon atoms) or trifluoromethyl and $n$ is 0 or an integer from 1 to 3. The substituents of R may be the same or different halogen atoms. Likewise, when $n$ is 2 or 3, X may be the same or different substituents from the above-described group.

Preferably R is alkyl of 1 to 2 carbon atoms substituted with 1 to 5 halogen atoms, preferably chlorine, or alkenyl of 2 carbon atoms (vinyl) substituted with 1 to 3 halogen atoms, preferably chlorine.

X is preferably halogen or nitro, and more preferably $n$ is 0.

Preferably R is perchloromethyl, trichlorovinyl or tetrachloroethyl, and more preferably perchloromethyl or 1,1,2,2-tetrachloroethyl.

Representative compounds of the present invention are:

3-(trichloromethylthio)-1,2,3-benzoxathiazin-4-(3H)-one 2-oxide;
3-(tribromomethylthio)-1,2,3-benzoxathiazin-4-(3H)-one 2-oxide;
3-(trifluoromethylthio)-1,2,3-benzoxathiazin-4-(3H)-one 2-oxide;
3-(dichloromethylthio)-1,2,3-benzoxathiazin-4-(3H)-one 2-oxide;
3-(chloromethylthio)-1,2,3-benzoxathiazin-4-(3H)-one 2-oxide;
3-(1',1',2',2'-tetrachloroethylthio)-1,2,3-benzoxathiazin-4-(3H)-one 2-oxide;
3-(1',2'-dibromoethylthio)-1,2,3-benzoxathiazin-4-(3H)-one 2-oxide;
3-(1'-chloro-2',2'-dibromoethylthio)-1,2,3-benzoxathiazin-4-(3H)-one 2-oxide;
3-(3'-chloropropylthio)-1,2,3-benzoxathiazin-4-(3H)-one 2-oxide;
3-(trichlorovinylthio)-1,2,3-benzoxathiazin-4-(3H)-one 2-oxide;
3-(2'-chlorovinylthio)-1,2,3-benzoxathiazin-4-(3H)-one 2-oxide;
3-(1',1',2',2'-tetrachloroethylthio)-6-chloro-1,2,3-benzoxathiazin-4-(3H)-one 2-oxide;
3-(trichloromethylthio)-6-chloro-7-nitro-1,2,3-benzoxathizin-4-(3H)-one 2-oxide;
3-(trichloromethylthio)-5,6,7-trichloro-1,2,3-benzoxathiazin-4-(3H)-one 2-oxide;
3-(1',2',2'-tribromovinylthio)-7-cyano-1,2,3-benzoxathiazin-4-(3H)-one 2-oxide;
3-(1',1',2',2',2'penthachloroethylthio-8-trifluoromethyl-1,2,3-benzoxathiazin-4-(3H)-one 2-oxide.

METHOD OF PREPARTION

These compounds are prepared by sulfenylating an appropriately substituted 1,2,3-benzoxathiazin-4-(3H)-one 2-oxide with a sulfenyl halide.

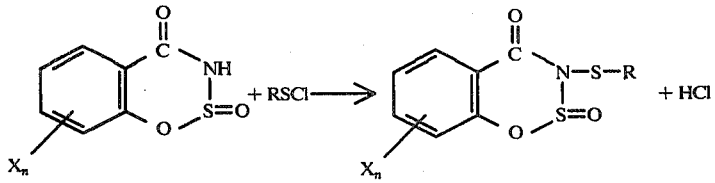

wherein R, X and $n$ are as previously defined.

The sulfenylation reaction is carried out by mixing essentially equimolar amounts of the reactants or up to 10% excess of the sulfenyl halide. This reaction is preferably carried out in a solvent such as methylene chloride, chloroform, acetonitrile, dimethoxyethane or dimethylformamide. The amount of solvent should be sufficient to dissolve the reactants, and usually is in the range of 2 to 10 times to volume of the reactants. For the best results, a basic material is added to the reaction mixture to remove the by-product HCl as it is formed. Such basic materials, also called "acid acceptors", include amines such as trimethylamine, triethylenediamine, quinuclidine, pyridine, quinoline, etc. The quantity of acid acceptor utilized is preferably sufficient to react with all of the HCl i.e., at least one equivalent of acceptor per mol of the sulfenyl halide employed.

The pressures and temperatures at which this reaction may be carried out are not critical. Temperatures are preferably in the range of ambient to the boiling point of the solvent employed, i.e., from about 20° C to 150° C. Pressures are usually atmospheric or autogenous, although higher and lower pressures may be used. The reaction will normally be completed in from ¼ to 2 hours.

The crude product of the reaction may be used in some instances as is, but preferably it is worked up to give the isolated compound. Usually the workup involves filtration and/or water washing to remove the hydrochloride salt and any unreacted sulfenyl halide. Then the solvent is removed by distillation, evaporation, or the like, to give a crude product which may be further purified, if desired, by recrystallization, distillation, or by passing over silica gel.

The 1,2,3-benzoxathiazin-4-(3H)-one 2-oxides are known compounds readily synthesized by the reaction of a salicylamide with thionyl chloride ($SOCl_2$) (ref. U.S. Pat. No. 3,780,030):

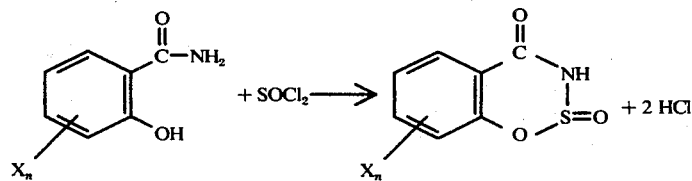

wherein X and n are as previously defined.

EXAMPLES

The present invention will be more fully understood by reference to the following examples, which illustrate method of preparation of the compounds of the present invention. The examples are in no way intended to limit the invention described herein unless otherwise indicated. Percentages are by weight.

EXAMPLE 1

Preparation of 1,2,3-benzoxathiazin-4-(3H)-one 2-oxide

A 500-ml, 3-necked flask equipped with a stirrer, condenser, dropping funnel, and thermometer was charged with 13.7 g (0.1 mol) of salicylamide, 13.1 g (0.11 mol) of thionyl chloride, and 200 ml of benzene. The resulting mixture was stirred at 75° C for 30 minutes. Then 210 ml of benzene was added, and the mixture was refluxed for 16½ hours.

Next the crude reaction mixture was cooled to about 5° C and filtered. The crystalline precipitate was washed with hexane and air dried to give 12 g of 1,2,3-benzoxathiazin-4-(3H)-one 2-oxide, m.p. 180°–182° C.

EXAMPLE 2

Preparation of 3-(trichloromethylthio)-1,2,3-benzoxathiazin-4-(3H)-one 2-oxide

A 300-ml flask equipped with a stirrer and thermometer was charged with 5.0 g (0.03 mol) of 1,2,3-benzoxthiazin-4-(3H)-one 2-oxide, 5.3 g (0.03 mol) of perchloromethyl mercaptan, 3.1 g (0.03 mol) of thiethylamine and 150 ml of methylene chloride. The resulting mixture was stirred at ambient temperature for 1 hour. At the end of this time, the reaction mixture was filtered and washed 3 times with equal amounts of water. After drying, the solvent was removed by evaporation. The crude product was passed through a 250-g silica-gel column using hexane, 10% ether/hexane, and 20% ether/hexane, respectively. Evaporation gave 4 g of 3-(trichloromethylthio)-1,2,3-benzoxathiazin-4-(3H)-one 2-oxide having a melting point of 65°–67° C.

Analysis for $C_8H_4Cl_3NO_3S_2$: Calculated, Cl, 31.98%; S, 19.28%. Found: Cl, 31.4%; S, 17.16%. An infrared spectra showed strong absorption at 1720, 1600, 1450, 1275, 1220, 1170, 1100, 1041, and 740 $cm^{-1}$.

EXAMPLE 3

Preparation of 3-(1',1',2',2'-tetrachloroethylthio)-1,2,3-benzoxathiazin-4-(3H)-one 2-oxide This reaction was carried out the same as in Example 2, except that the perchloromethyl mercaptan was replaced by 1,1,2,2-tetrachloroethyl sulfenyl chloride. The crude reaction mixture was washed, dried, and evaporated to give 4.4 g of the desired compound, having a melting point of 96°–99° C.

Analysis for $C_9H_5Cl_4NO_3S_2$: Calculated, Cl 37.22%; S, 16.83%. Found: Cl, 33.7%; S, 15.4%. The infrared spectra showed strong absorption at 1700, 1600, 1450, 1370, 1280, 1230, 1200, 1160, 1040, 740, and 700 $cm^{-1}$.

EXAMPLE 4

Preparation of 3-(trichlorovinylthio)-1,2,3-benzoxathiazin-4-(3H)-one 2-oxide

This reaction was carried out essentially the same as Example 3, except that the tetrachloroethyl sulfenyl chloride was replaced by trichlorovinyl sulfenyl chloride. The product, 4.8 g, had a melting point of 91° C. Analysis for $C_9H_4Cl_3NO_3S_2$: Calculated, Cl, 30.86%; S, 18.61%. Found: Cl, 28.8%; S, 18.4%. The infrared spectra showed strong absorption at 1680, 1450, 1370, 1280, 1230, 1200, 1170, and 1100 $cm^{-1}$.

UTILITY

The compounds of the invention are useful for controlling fungi, particularly plant fungal infections caused by *Botrytis cinerea*, leaf blights caused by organisms such as *Erysiphe polyqoni* and *E. chicoraciarum*, and other fungal infections caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophrone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

Fungicidal tests on compounds of the present invention were made using the following methods.

EXAMPLE A

Tomato Early Blight

The compounds of Examples 3 and 4 of the invention were tested for the control of the Tomato Early Blight organism, $Alternaria\ solani\ conidia$. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compound of Example 3 showed 33% control and the compound of Example 4 showed 84% control. The compound of Example 2 was inactive.

EXAMPLE B

Botrytis cinerea control

The compound of Example 2 of the invention and Compound 1 (prior art compound) were tested for $Botrytis\ cinerea$ control using detached, well-developed primary leaves of a 4–6 week old horsebean plant. The leaves were dipped into a 40-ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of $Botrytis\ cinerea$ fungus grown on potato dextrose agar plates. The plates were covered after inoculation and kept at 23.5° C. The filter-paper linings of the plates were kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. Similar tests were also made using 16-ppm solution of the compound and 6.4-ppm solution. The compound of Example 2 exhibited 34–45% control at the 40-ppm level, 26% control at the 16-ppm level and 28% control at the 6.4-ppm level. The compound of Example 1, while exhibiting 16–56% control at the 40-ppm level, exhibited 0% control at the 16% and 6.4% levels. The compounds of Examples 3 and 4 were also tested for $Botrytis\ cinerea$ control and were not found to be useful for this fungus.

EXAMPLE D

Mycelial Inhibition

The compound of Example 3 of the present invention was evaluated and found fungicidally effective by means of a mycelial inhibition test. This test is designed to measure the fungitoxic activity of fungicidal chemicals in terms of their degree of inhibition of mycelium growth. The compound was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a micro sprayer with the fungicidal solution. The treated paper strips were incubated at 25° C and data is taken after 24 hours. Fungicidal activities are measured by a zone of inhibited mycelial growth from the center of the paper strip.

The compound of Example 3 showed the following activity measured in terms of the microgram/cm² for 99% control of the fungus:

| | |
|---|---|
| Pythium ultimum | 0.37 |
| Rhizoctonia solani | 0.37 |
| Aspergillus niger | >1.7 |
| Fusarium moniloforma | 0.63 |

As will be evident to those skilled in the art, various modifications of this invention can be made or followed in the light of the foregoing disclosure, without departing from the spirit or scope of the disclosure or from the scope of the following claims.

What is claimed is:

1. A compound of the formula

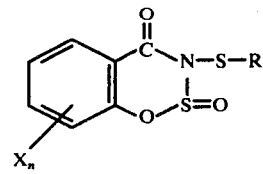

wherein R is an alkyl group of 1 to 3 carbon atoms substituted with 1 to 5 halogen atoms of atomic number 9 to 35 or an alkenyl group of 2 to 3 carbon atoms substituted with 1 to 5 halogen atoms of atomic number 9 to 35; X is halogen of atomic number 9 to 35, nitro, cyano, alkyl of 1 to 4 carbon atoms, alkoxy of 1 to 4 carbon atoms or trifluoromethyl and $n$ is 0 or an integer from 1 to 3.

2. The compound of claim 1 wherein R is alkyl of 1 to 2 carbon atoms substituted with 1 to 5 halogen atoms or allyl substituted with 1 to 3 halogen atoms.

3. The compound of claim 2 wherein the halogen atoms are chlorine.

4. The compound of claim 1 wherein R is trichloromethyl, trichlorovinyl or tetrachloroethyl and n is 0.

5. The compound of claim 4 wherein R is 1,1,2,2-tetrachloroethyl.

6. A fungicidal composition comprising a fungicidally effective amount of the compound of claim 1 and an inert carrier.

7. A method for controlling fungi which comprises contacting said fungi with a fungicidal amount of the compound of claim 1.

* * * * *